(12) United States Patent
Hirai

(10) Patent No.: US 6,789,019 B2
(45) Date of Patent: Sep. 7, 2004

(54) CLINICAL-EXAMINATION-NUMERICAL-DATA-PROCESSING SYSTEM AND RECORDING MEDIUM FOR DIAGNOSTIC PROGRAM USING THE SYSTEM

(76) Inventor: Toshihiro Hirai, 1-2375-1, Sayama, Osakasayama-shi, Osaka (JP)

(*) Notice: Subject to any disclaimer, the term of this patent is extended or adjusted under 35 U.S.C. 154(b) by 456 days.

(21) Appl. No.: 09/824,632

(22) Filed: Apr. 4, 2001

(65) Prior Publication Data

US 2002/0077755 A1 Jun. 20, 2002

(30) Foreign Application Priority Data

Apr. 7, 2000 (JP) ........................................ 2000-106064

(51) Int. Cl.$^7$ ............................................... G06F 19/00
(52) U.S. Cl. ....................................................... 702/19
(58) Field of Search ........................................... 702/19

(56) References Cited

U.S. PATENT DOCUMENTS 3,811,040 A * 5/1974 Weinfurt et al.

* cited by examiner

Primary Examiner—John S. Brusca
(74) Attorney, Agent, or Firm—Rothwell, Figg, Ernst & Manbeck

(57) ABSTRACT

A clinical-examination-numeral-data-processing system is constituted in which a plurality of laboratory observed values presented by items are transformed into positive and negative finite integers making observed values, including limitless values, the unit inside the interval of boundary values decided arbitrarily and they are ranked and processed according to the degree of importance on diagnosis, and it is made possible to perform transformation process for transforming a plurality of laboratory observed data presented by items being expressed by different units into the data being expressed with a comparable standardized unit, and to compose the transformed values of laboratory observed values to a list by examination items.

5 Claims, 6 Drawing Sheets

| RECORD COUNT | | | | | | | |
|---|---|---|---|---|---|---|---|
| NUMBER OF DATA | REFERENCE VALUE | | SAMPLE PICKING DATE AND MEASURED DATA | | | | |
| UNIT | LOWER-LIMIT | UPPER-LIMIT | ITEM TITLE | | | | |
| 45 | | | Y/M.D | 97 | 97 | 97 | 97 |
| UNIT | L | U | 2>BIOCHEM I | 10.08 | 10.21 | 11.04 | 11.11 |
| g/dL | 3.5 | 4.8 | Alb | 2.9 | 3.4 | 3.2 | 2.9 |
| mg/d | 0.2 | 1.1 | T-bil | 0.2 | 0.3 | 0.2 | 0.2 |
| mg/d | 0.1 | 0.5 | d-bil | 0.1 | | 0.1 | |
| K-U | 1 | 13 | ZTT | 12.7 | 12.9 | 6.2 | 5.2 |
| K-U | 0 | 4 | TTT | 3.4 | 3.5 | 0.6 | 1.1 |
| U/L | 124 | 354 | ALP* | 258 | 254 | 281 | 237 |
| IU/L | 209 | 481 | CholE* | 374 | 442 | 495 | 465 |
| IU/L | 36 | 87 | LAP* | 134 | 227 | 219 | 181 |
| U/L | 9 | 31 | GOT | 19 | 30 | 22 | 20 |
| U/L | 4 | 34 | GPT | 18 | 48 | 23 | 20 |
| ratio | 0.62 | 2.67 | GOT/GPT | 1.06 | 0.63 | 0.96 | 1 |
| U/L | 0 | 47 | γ-GTP* | 39 | 105 | 84 | 59 |
| U/L | 255 | 474 | LDH | 1277 | 1487 | 1345 | 1051 |
| IU/L | 1.7 | 6.2 | ALD | 5.7 | | 7.3 | |
| U/L | 53 | 288 | CPK* | 94 | | 30 | |
| IU/L | 50 | 185 | S-AMY | 111 | 137 | 143 | 118 |
| mg/d | 60 | 110 | S-Glu | 123 | 148 | 71 | |
| mg/d | 3 | 7 | UA* | 3.3 | 4.1 | 2.5 | 2.5 |
| mg/d | 7 | 22 | BUN | 29 | 44.9 | 15 | 14.5 |
| mg/d | 0.4 | 1.1 | CRE | 1.9 | 1.2 | 1.3 | 1.4 |
| mg/d | 123 | 236 | tChol | 88 | 141 | 154 | 149 |
| mg/d | 39 | 158 | TGL | 172 | 144 | 109 | 287 |
| mg/d | 41 | 68 | HDL-C | 14 | 38 | 25 | 21 |

FIG. 1

COMPUTER SCREEN

| Y/M.D | 97 | 97 | 97 | 97 |
|---|---|---|---|---|
| 2>BIOCHEM I | 10.08 | 10.21 | 11.04 | 11.11 |
| Alb | -19 | -12 | -15 | -19 |
| T-bil | -10 | -8 | -10 | -10 |
| d-bil | -10 |  | -10 |  |
| ZTT | 10 | 10 | -1 | -3 |
| TTT | 7 | 8 | -7 | -5 |
| ALP | 2 | 1 | 4 | 0 |
| CholE | 2 | 8 | 12 | 9 |
| LAP | 26 | 41 | 40 | 35 |
| GOT | -1 | 10 | 2 | 0 |
| GPT | -1 | 19 | 3 | 1 |
| GOT/P | -6 | -10 | -7 | -7 |
| γ-GTP# | 9 | 21 | 18 | 13 |
| LDH | 45 | 47 | 46 | 40 |
| ALD | 8 |  | 15 |  |
| CPK | -7 |  | -12 |  |
| S-AMY | -1 | 3 | 4 | 0 |
| S-Glu# | 15 | 24 | -6 |  |
| UA | -9 | -5 | -13 | -13 |
| BUN | 19 | 33 | 1 | 0 |
| CRE | 29 | 13 | 16 | 18 |
| tChol | -16 | -7 | -5 | -6 |
| TGL | 13 | 8 | 2 | 28 |
| HDL-C | -27 | -13 | -21 | -23 |

FIG. 2

| L | U | 2>BIOCHEM I | 03.25 | 42 | 196 | S-Fe | 102 |
|---|---|---|---|---|---|---|---|
| 3.5 | 4.8 | Alb | 3.9 | 141 | 341 | UiBC | 167 |
| 0.2 | 1.1 | T-bil | 0.16 | 274 | 431 | TiBC | 269 |
| 0.1 | 0.5 | d-bil | 0.08 | 135 | 149 | Na | 136 |
| 1 | 13 | ZTT | 8.5 | 3.5 | 5 | K | 5.5 |
| 0 | 4 | TTT | 67.8 | 96 | 108 | Cl | 103 |
| 124 | 354 | ALP* | 343 | 41 | 71 | Sial A | 70 |
| 209 | 481 | ChoIE* | 561 | 30 | 60 | %Fe-sat | 37.9 |
| 36 | 87 | LAP* | 77 | -1 | 1 | *inf-V | 0 |
| 9 | 31 | GOT | 21 | 276 | 292 | *Bl Os P | 297 |
| 4 | 34 | GPT | 16 | 0.009 | 0.123 | GOT/LDH | 0.032 |
| 0.62 | 2.67 | GOT/GPT | 1.31 | 0 | 5 | LDH/GOT | 31.7 |
| 0 | 47 | γ-GTP* | 100 | 45.6 | 139.2 | LDL-C | 33 |
| 255 | 474 | LDH | 665 | 95 | 180 | eChol | 112 |
| 1.7 | 6.2 | ALD | 7.3 | 190 | 500 | β-LP* | 435 |
| 53 | 288 | CPK* | 118 | 157 | 273 | PLP | 244 |
| 50 | 185 | S-AMY | 83 | 105 | 801 | FFA | 80 |
| 60 | 110 | S-Glu | 81 | 110 | 209 | HBDH | 410 |
| 3 | 7 | UA* | 3.7 | L | U | 3>URINOUS BIOCHEM | 03.29 |
| 7 | 22 | BUN | 27.3 | 1.006 | 1.002 | SG | 1.012 |
| 0.4 | 1.1 | CRE | 2 | 5.5 | 6.8 | PH | 5 |
| 123 | 236 | tChol | 231 | 0 | 0.48 | Prot | 2 |
| 39 | 158 | TGL | 1036 | -10 | 10 | Pr<mg<dl | 100 |
| 41 | 68 | HDL-C | 32 | -0.48 | 0.48 | Sug | 0 |
| 0 | 10.2 | Ca | 10.1 | | | Sg<mg<dl | |
| 2.8 | 4.8 | inP | 3.5 | 0.5 | 1 | UroBlg | 0.5 |
| 1.7 | 2.4 | Mg | 2.6 | 0 | 1 | Bil | 0 |

FIG. 3

| 2>BIOCHEM I | 03.25 | S-Fe | -2 |
|---|---|---|---|
| Alb | -4 | UiBC | -8 |
| T-bil | -11 | TiBC | -11 |
| d-bil | -11 | Na$ | -9 |
| ZTT | 3 | K$ | 18 |
| TTT | 56 | Cl | 2 |
| ALP | 10 | Sial A | 10 |
| CholE | 16 | %Fe | -5 |
| LAP | 6 | *inf-V | |
| GOT | 1 | *Bl Os P | 16 |
| GPT | -2 | GOT/LDH | -6 |
| GOT/P | -4 | LDH/GOT | 49 |
| γ-GTP# | 21 | LDL-C | -13 |
| LDH | 25 | eChol | -6 |
| ALD | 15 | β-LP | 6 |
| CPK | -5 | PLP | 5 |
| S-AMY | -5 | FFA | -11 |
| S-Glu# | -2 | HBDH | 37 |
| UA | -7 | 3>URINOUS BIOCHEM | 03.29 |
| BUN | 17 | SG | -3 |
| CRE | 30 | PH | -18 |
| tChol | 10 | Prot | 43 |
| TGL | 52 | Pr<mg<dl | 47 |
| HDL-C | -17 | Sug | 0 |
| Ca | 9 | Sg<mg<dl | |
| inP | -3 | UroBlg $ | 0 |
| Mg | 16 | Bil | 0 |

FIG. 4

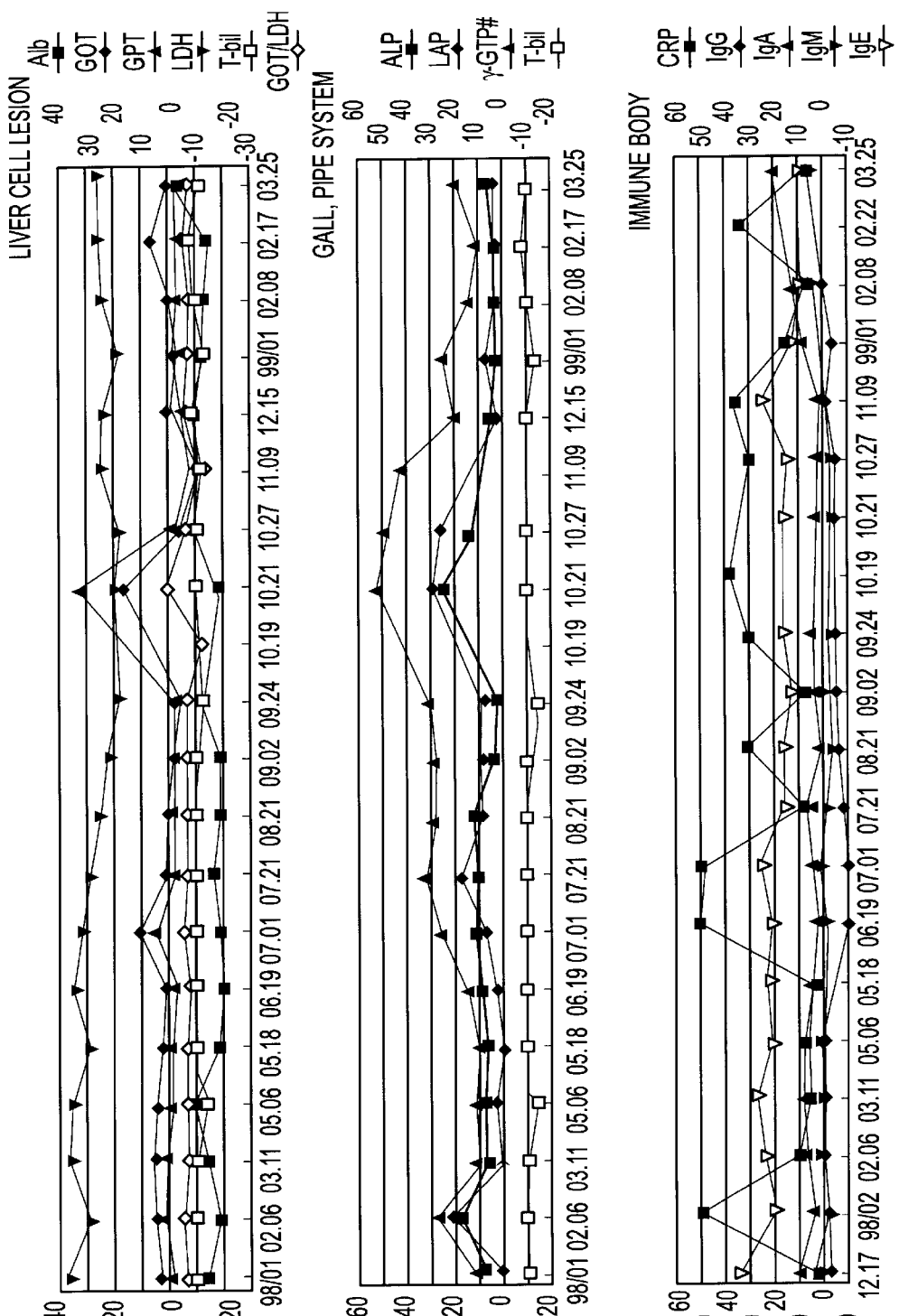

CLINICAL-EXAMINATION-NUMERICAL-DATA-PROCESSING SYSTEM AND RECORDING MEDIUM FOR DIAGNOSTIC PROGRAM USING THE SYSTEM

BACKGROUND OF THE INVENTION

The present invention relates to a clinical-examination-numerical-data-processing system which is needed by clinicians for the diagnosis of the diseases of patients, the causes of the diseases, the condition of diseases and the state of the diseases, and further for the selection of curative means and for the judgment of curative values at their job sites of clinical-medical treatments, and a recording medium for storing diagnosis programs using the above system.

In the past, the test results which are reported from a clinical laboratory or a clinical diagnostic test manufactures to a doctor in charge of a patient is composed of a variety of numerical data, and they are accompanied by a group of reference interval by the units adopted by respective manufactures composed of lower limits and upper limits obtained by statistically processing the measured data on healthy persons for examination items.

It is a great labor for a clinician facing a patient to perform evaluation and to proceed diagnosis with reference to inherent reference values by items, and also referring to many items, ranging to the past, and to the data of several kinds of items to be combined in every differential-diagnostic disease or further to the items to be revised from the result of re-examination, and it might happen to overlook an important synthetic view caused by the burden as heavy as that.

It is necessary to transform and process the total data into a single finite series to make the necessary information from the point of view of a clinician be read out easily and to make the read out information be useful for clinical judgment. For that purpose, a standardized expression method of respective clinical-examination-numerical data (observed values) had been proposed several times in the past; however all of them have had their limits, and at present no one actually uses these proposals being unable to satisfy the requests of the clinical world.

SUMMARY OF THE INVENTION

The present invention is intended to cope with the above-mentioned problems and the invention has been developed as a clinical-examination-numerical-data-processing system, wherein a plurality of pieces of laboratory observed values presented for each item are transformed into positive and negative finite integer values in which a reference value is set as a unit within a range of threshold values decided arbitrarily, and said transformed values are ranked according to the degree of importance on diagnosis for processing.

The present invention provides a computer-readable recording medium storing a program to make a computer execute a transformation process for transforming a plurality of pieces of laboratory observed values expressed by different kinds of numerical units and presented for each item into comparable data expressed in one unit, and a display process for displaying the transformed values of observed values in a list for respective inspection items, for evaluating diagnostically by the distance from the reference-transformed value and for applying different colors for respective ranks to numeral columns showing results, in order that a plurality of pieces of observed values presented by examination-items to a clinician at his job site can be immediately processed by the above-mentioned processing system and reflected on the diagnosis.

In the observed-values-transformation equations developed by the inventor of the present invention, a symbol "*" means a multiplying symbol x and to avoid the confusion with data x "*" is used. The same thing is true in the following equations. The following equations are identical to the equations, 1, 2, and 3 described in claim 2. The observed values x are presented together with the upper limit value (U) and the lower limit value (L) shown by healthy and normal people, so that (U−L)>0, and the transformed reference-lower-limit value and reference-upper-limit value correspond to $-H_U$, $H_U$ respectively. The value after transformation: for P which designates from—infinity to +infinity, in the case where the above value is to be continuously transformed between the two values (−P and P), $H_1(x)$, $H_2(x)$ and $H_3(x)$ described in claim 2 can be expressed simply as shown below, $$H_1(x) = \frac{2P}{\pi} * \mathrm{Tan}^{-1}\left\{\mathrm{Tan}\left[\frac{\pi}{2P} * H_U\right] * \frac{2f(x) - f(U) - f(L)}{f(U) - f(L)}\right\} \quad \text{Eq. 4}$$

$$H_2(x) = P * \mathrm{Tanh}\left\{\mathrm{Tanh}^{-1}\left[\frac{H_U}{P}\right] * \frac{2f(x) - f(U) - f(L)}{f(U) - f(L)}\right\} \quad \text{Eq. 5}$$

$$H_3(x) = \frac{1}{2} * \left[\left|H_U * \frac{2f(x) - f(U) - f(L)}{f(U) - f(L)} + P\right| - \left|H_U * \frac{2f(x) - f(U) - f(L)}{f(U) - f(L)} - P\right|\right] \quad \text{Eq. 6}$$

When a function in which a real number X is rounded to the nearest integer is expressed by Round(X,0), then a transformation function G(x) can be expressed by Eq. 7.

$$G(x) = \mathrm{Round}\{H_i(x), 0\} \quad \text{Eq. 7}$$

where "i" means 1,2 or 3

Since $H_i(x)$ is defined by $-P \leq H(x) \leq P$, and disregarding the f(x), it passes always two points, $(L, -H_U)$ and $(U, H_U)$, and other points than these two points are decided by f(x).

Since $H_i$ contains a function f(x), which can be arbitrarily selected, in its inside, it is defined to be a frame function H.

The transformed values of observed values by H function are further transformed to a nearest integer by rounding. The rounded values G(x) are defined as general-clinically-evaluated values (G-values). The transformation is defined as G-transformation.

By the utilization of the G-transformation to the standardized expression of the clinical-examination-numerical data, the maximum value and the minimum value become symmetry with respect to 0 and have the same absolute value of finite value and thereby it is made possible to express the transformed values corresponding to the critical values in the reference region (reference values) with integers of the same value.

BRIEF DESCRIPTION OF THE DRAWINGS

FIG. 1 shows a list in which biochemical-examination items (ALB, T-bil, d-bil, ZTT, - - - ) are shown approximately at the center, on the left side the unit of the conventional-observed value, the lower-limit value and the upper-limit value to be reference values are shown, and on the right side specimen-collected date at the top row and measured data are shown as samples;

FIG. 2 shows an embodiment according to the present invention, showing a computer screen in which numerical data shown in FIG. 1 are G-transformed and expressed with G-values;

FIG. 3 shows a list showing the newest data for diagnosis as samples similar to those shown in FIG. 1;

FIG. 4 shows an embodiment according to the present invention showing a computer screen in which the numerical data shown in FIG. 3 are G-transformed and expressed with G-values.

DETAILED DESCRIPTION OF THE PREFERRED EMBODIMENTS

Figure 5A:
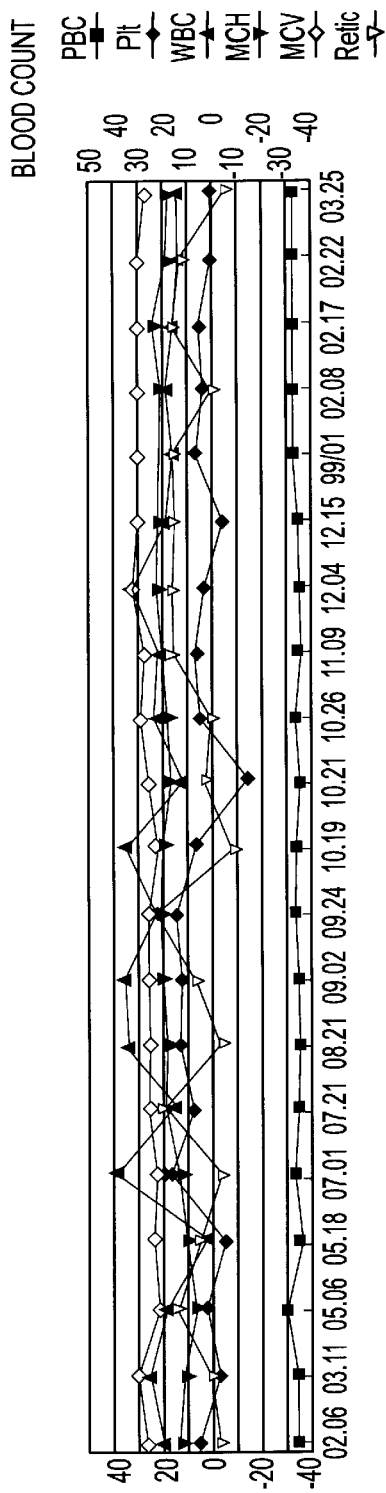
FIG. 5 shows an embodiment in which the change with the passage of time of clinical-examination-numerical data. The figures, expressed on a computer screen, are depicted with G values of test groups, titled respectively by blood cell count, the image of white corpuscles, liver-cell lesion, the gall, the pipe system and an immune body of a patient; and shows a graph in which the interval of transformed numerical values, −60 to 60, reference limit(s) (lower limit and/or upper limit) being made to correspond to −10 and 10 respectively, and G-values rounded to the nearest integers are shown in the axis of ordinates, and in the axis of abscissas, a part of a time series is taken up as samples from 6 Feb. 98 to 25 May 99. The graph is expressed by polygonal lines having different colors from each other, and each polygonal line expresses each of these examination items.

An embodiment according to the present invention will be explained in the following. The range of numbers to be transformed will be assumed to be from −60 to 60, and reference values (lower limit and upper limit) are made to correspond to −10 and 10, and they are rounded to nearest integers.

In a case where only the upper limit value is shown as a reference ($x \leq U$), the lower limit value is regarded to be 0, and in a case where only the lower limit value is shown ($x \geq L$ as the reference interval), the lower limit value will be decided to be greater than −10 and the observed value 0 will be made to −60.

In order to apply G(x)-function to the actual clinical-examination -numerical-data process, further depending on the fact that whether the boundary values presented as a reference limit value are included in the reference interval or not, there are 4 cases in the type (type-a) where the reference interval is placed between 2 numbers, and there are 2 cases respectively in the type (type-b) where only upper limit is shown and in the type (type-c) where only lower limit is shown, and when the frame function $H_1$ is taken up as a model, the frame function $H_1$ and constants are put in order as shown in Table 1.

From the seventh line to the ninth line show G-transformed values given by boundary values (L, U or 0) based on the types of operators.

For the above system, $\{(-60, 60), (-10, 10)\}$ in the format of $\{$(minimum value, maximum value), (reference-interval lower limit, reference-interval upper limit)$\}$, a counterproposal $\{(-63, 63), (-9, 9)\}$ can be considered; however in that case, all work to be done is only the change in constants, and the form of the H-frame-function expression is identical.

In a case where the results of measurements or observations are expressed in the form of, −, +, ++, - - - 5+, the case can be considered to be in the category of type-b, and the input x in each case is put 0, 1, 2, - - - 5, and utilizing Eq. 8, G-values are transformed into 0, 20, 30, 40, 50 and 60.

$$G(x) = 10 * \left\{1 - Int\left[\frac{1.999}{1+|x|}\right]\right\} * (Int(|x|) + 1) * Int\left[\frac{11.999}{6+|x|}\right] \qquad \text{Eq. 8}$$

(In Eq. 8, when the absolute value of an input is more than 6, 0 is given in place of the input and the input having (−) sign or a small number of misinput is ignored). In the case of an examination where only 2 values (−and +) are taken, it is proper to transform an input, (0 and 1), to (0 and 30).

For special examples such as the quantity of urobilinogen contained in one's urine (There are (+), (±) and (−) in the quantity of it, and in the case of (−) value and that of (+) value have quite different diagnostic meaning and different degree of seriousness.) or Gaffky (0 to 10), a special transforming equation unique to the item shall be used.

Further, let the clinical evaluation (for example, a degree of seriousness) of respective cases, too high abnormal values and too low abnormal values by examination items, be expressed by the standardized absolute value G ($|G(x)|$).

In order to realize the above idea, if a degree of a clinical symptom or a clinical evaluation (the degree of seriousness, etc.) at a certain point of measurement $X_1$ in an area exceeding a reference boundary value on a side is in the same order as that at a certain point of measurement $X_2$ in an area exceeding a reference boundary value on another side, absolute values of the same order must be given to them as G-values of respective data. It is possible by selecting the type of the $H_f(x)$ and f(x) properly.

For the purpose of making a new inspection list ranging over a variety of items and a large number of G-values measured in the past easier to read out and easier to utilize for judgment, the form of expression of G-values on a

TABLE 1

| Type | Type-a | | | | Type-b | | Type-c | |
| --- | --- | --- | --- | --- | --- | --- | --- | --- |
| $H_1$ (X) | $\alpha * Tan^{-1}\left\{K_1 * \frac{2f(x) - f(U) - f(L)}{f(U) - f(L)} + K_2\right\}$ | | | | $\alpha * Tan^{-1}\left\{K_1 * \frac{f(x) - f(0)}{f(U) - f(0)}\right\}$ | | $\alpha * Tan^{-1}\left\{K_1 * \frac{f(x) - f(0)}{f(L) - f(0)} + K_2\right\} - 30$ | |
| Operator | $L \leq x \leq U$ | $L < x < U$ | $L \leq x < U$ | $L < x \leq U$ | $[0] \leq x \leq U$ | $[0] \leq x < U$ | $L \leq x$ | $L < x$ |
| α | 38.1972 | 38.1972 | 38.1972 | 38.1972 | 38.1972 | 38.1972 | 25.4648 | 25.4648 |
| K1 | 0.282001 | 0.282312 | 0.28209 | 0.282029 | 0.282001 | 0.282312 | 3.376448 | 3.374936 |
| K2 | 0 | 0 | 0.000283 | −0.000283 | None | None | −2.414211 | −2.414211 |
| G (L) | −10 | −11 | −10 | −11 | None | None | −10 | −11 |
| G (U) | 10 | 11 | 11 | 10 | 10 | 11 | None | None |
| G (0) | Indefinite | Indefinite | Indefinite | Indefinite | 0 | 0 | −60 | −60 |

The second line shows transforming expressions corresponding to the reference-value types shown in the first line, the third line shows the types of operators, from the fourth line to the sixth line show the values of constants in the formulas of respective types shown in the third line.

computer screen utilizes different forms of characters and different colors for the discrimination of the ranges of G-values; for example, negative numbers less than −11 are italicized and the order of coloring of respective groups of G-values on the computer screen is set as shown in Table 2.

TABLE 2

| | | Data base | | Newest data list: no measurement on the displayed data | |
|---|---|---|---|---|---|
| Level | Range of absolute G-value | Background color | Character size and color | Background color | Character size and color |
| 0 | 0~10 | Sky-blue | Fine, black | White | Fine, sky-blue (thick) |
| 1 | 11~15 | Green | Bold, black | White | Bold, green |
| 2 | 16~25 | Yellow | Bold, black | White | Bold, orange |
| 3 | 26~35 | Pink | Bold, black | White | Bold, pink |
| 4 | 36~45 | Red | Bold, void | White | Bold, red |
| 5 | 46~55 | Purplish red | Bold, void | White | Bold, purplish red |
| 6 | 56~60 | Dark blue | Bold, void | White | Bold, dark blue |

The H-frame function means a function which shuts up real numbers from +infinity to −infinity in a specific finite range, and it is developed by the inventor of the present invention independently. The function passes through predetermined 2 points and contains function f(x) by which the other points can be freely selected.

A G-value for x within the reference interval can be clinically considered to show approximately normal values, so that the change in the value or a large or small value within the reference interval is not considered to be an important comparison target. Therefore, in an interval where a measured value exceeds the reference limit values, by proper selection of an arbitrary function f(x), it is made possible to give a specified G-transformed value, that is a clinical-evaluation indication, to a specified measured value x by items.

In other words, in contrast with the conventional idea, the degree of clinical evaluation having clinical significance such as diagnosis final value, etc. are allotted to G-values and it is made possible to retrieve and decide a function f(x) so that measured values x being clinically significant give the G-values by examination-items. As an example, the correspondence between the clinical symptoms and diagnosis by observed values (unit: mg/dL) for the density of serum glucose and the change in G-value when the internal function f(x) is applied as shown

TABLE 3

| Serum glucose | | G-value* | |
|---|---|---|---|
| mg/dL | Symptom and Diagnosis | f (x):x | :Ln(x − 5) |
| 10 | Irreversible change in total internal organs | −32 | −56 |
| 20 | Convulsions, loss of consciousness | −28 | −46 |
| 35 | Cold sweat, Zyanose, symptoms in automatic nervous system | −23 | −31 |
| 50 | Light mental symptoms, central nervous system symptoms | −15 | −18 |
| 60 | At empty stomach reference lower limit | −10 | −10 |
| 100 | At empty stomach reference upper limit | 10 | 10 |
| 120 | Diabetes diagnostic value (WHO) | 19 | 17 |
| 200 | Final diagnostic value | 47 | 34 |
| 300 | | 58 | 43 |
| 400 | | 59 | 48 |

*For H(x), Hyperbolic tangent H2 (x) = 60 * Tanh{Tanh$^{1}$10 · 49/60)/(f(U) − f(L) * (2f(x) − f(U) − f(L)}) was used.

Table 3 shows that when Ln(x−5) (Ln: natural logarithm) is introduced for f(x), the reference G-values (−10, 10) are given for the reference values (lower limit 60, upper limit 100). In the case of {f(x)=x} denoted in the third column, the clinical-generalized evaluation shown by absolute G-values lie on both sides exceeding reference limit values, and they are dislocated far from clinical significance, but in the case where {f(x)=Ln(x−5)} is introduced, as shown in the fourth column of the Table 3, the result approximately coincides with the generalized evaluation.

When the function f(x) thus obtained is used in every examination item, the transformed G-values can be immediately the evaluation value corresponding clinically to the degree of seriousness or the grade of diagnosis.

FIG. 1 shows 245 items of examinations, picked up from clinical-examination data ranging from 1995 over to 1999. On the left side of the biochemical examination titles (Alb, T-bil, d-bil, ZTT - - - ), positioned approximately at the center, the unit of conventional laboratory observed values, reference-lower-limit values and reference-upper-limit values are shown, and on the right side, specimens collected dates at the top row and observed values are shown, and observed values specimens-collected and measured on 8 Oct., 21 Oct., 4 Nov., 11 Nov. '97 are shown in the lower part of the column.

When these data are G-transformed and displayed on the computer screen, the pattern on the screen becomes as shown in FIG. 2. In the range (−35 to 35), characters are colored with a predetermined color (black), backgrounds are: (within reference area) (−10 to 10): sky-blue, (reexamination, observation, referring other data or items) (−15 to −11, 11 to 15): green, (abnormal, precise examination and diagnosis) (−25 to −16, 16 to 25): yellow, (systemic examination and start of medical treatment) (−35 to −26, 26 to 35): pink, hereinafter with reversed characters, (hospital treatment) (−45 to −36, 36 to 45): red, (urgent treatment, or tumor-like) (−55 to −46, 46 to 55) purplish red, (tumor-like) (−60 to −56, 56 to 60): dark blue.

FIG. 3 shows the newest data list for the present-disease diagnosis similar to those shown in FIG. 1, and in a case where measurement was not made on the described date, the newest data before the date are displayed. When these data are G-transformed and displayed on a computer screen with G-values, a very compact list is displayed as shown in FIG. 4.

About the allotment of the significance of clinical medicine to the G-values, the following procedures will be considered: the first step will be the definition by an international committee level and the second step will be the decision of G-values for the final diagnosis values x on every item by specialists in clinical medicine in various districts, and then the optimum function f(X) will be decided.

In other words, H-frame function has capability of extension to the numerical values for giving data-evaluation values on clinical medicine, or to the final-diagnosis-index number for a disease caused by a combination of items.

When the inspection results are displayed with the use of G-values constituted as shown in the above, there is no need to describe reference values and the unit being used, and the characters to be displayed become only G-values being constituted with less than 3 characters including a (−) sign, and thereby the newest examination results of more than 200 can be displayed in a list.

In the result, it is made possible to display the results of all necessary items for a patient such as those in biochemistry (including genetics), immunology, inflammation field on a computer screen, so that the read-out of data of examination items to be a combination set, the data which are necessary for every disease on which differential diagnosis is to be performed, can be performed dispensing with the retrieval at the place where the information of an item exists.

The display on a screen, when a specific color is given to numerical values and backgrounds belonging to each group of absolute G-values, the read-out of general-clinical significance will be made easier, and also it will be made easier to read the change in the condition of a disease with the passage of time being able to observe all data on a list (FIG. 2).

As shown in Table 2, in the higher level than level 4, that is, in the more serious stage than hospital treatment, reversed characters are used to show that it is an important turning point on the diagnostic keynote. In the table showing the newest measurement results that is shown in FIG. 4, about an item which was not measured on the described specimen-collected date, the last data can be displayed in a different expression, which may help diagnostic judgment.

As mentioned above, a specific color is given to each group of numerical values; thereby it is made possible to take out an item immediately in the order of the degree of abnormality, thus judgment can be done at a glance, which enables to avoid an overlook almost, the overlook which may apt to occur when judged by only numerals by far from observed values expressed real numbers.

When the values corresponding to clinical-evaluation values or the degree of seriousness, the level of diagnosis (treatment as an outpatient, treatment as an inpatient, urgent hospitalization, etc.) are allotted to G-values and a proper internal function is decided, further quick and certain diagnosis will be realized.

Owing to the present invention, G-values are standardized as positive and negative integers making a reference limit value the basic unit, and now it is not needed for clinicians to memorize or describe a reference value of certain laboratory observed data, and as far as the standard value conforms to the standards decided by NCCLs (National Committee for Clinical Laboratory standards), the troubles caused by the unit in observed values, or the change in the reference value or in the method of measurement by clinical laboratories can be avoided.

By the distribution of respective groups of observed values on all items in a common and finite range, it was made possible to display graphs of a plurality of polygonal lines in a single coordinate system for the first time. It is made possible to display especially the changes in arbitrarily selected several items with the passage of time can be displayed on a single coordinate system on a screen, therefore not only the grasp of the course of a disease but also the mutual relation between the conditions in the past and those at the present can be read at a glance.

In the result, the characteristic and constitution of a patient can be read, and also the differential diagnosis or the tendency of a disease can be more precisely perceived. And from the total data the state where a patient had been in healthy condition can be judged, further from the data in various items the probability has been generated to obtain the normal values of a patient (the amplitude of variation in his constitutional data in his healthy time) which has been considered to be ideal but to be impossible so far.

Figure 5B:
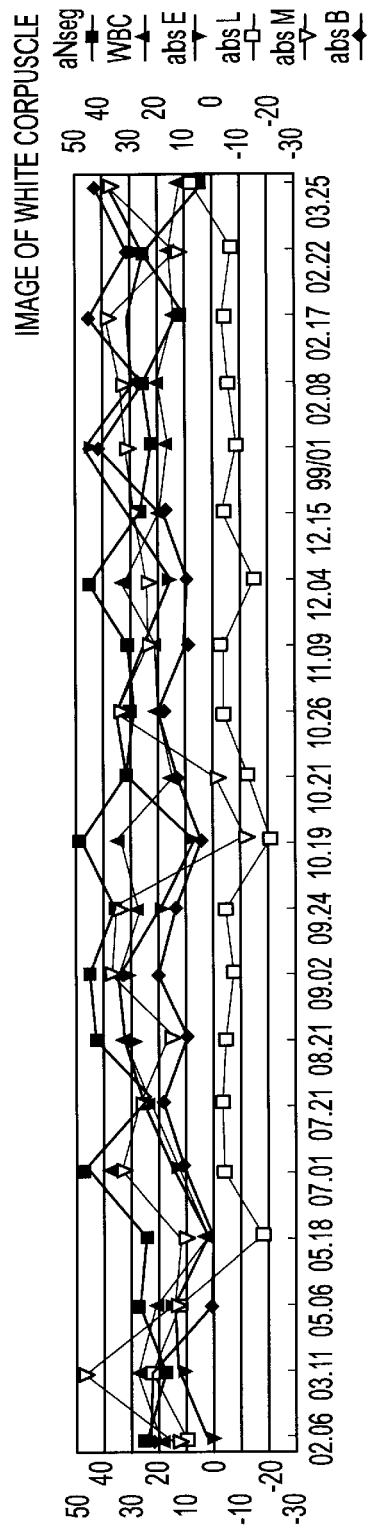

FIGS. 5A–5E show an example of a display of changes with the passage of time in the clinical examination items (for example, RBC, Pit, WBC, MCH, MCV, Retic on the blood cell count, images of white corpuscles, the liver cell lesion, the gall, the pipe system and the immune body) of a patient on a computer screen.

Thereby, the changes of respective data by items which had been shown by different units at a clinical examination stage can be displayed in a single coordinate system with the passage of time and also the mutual relations among the examination-data items can be read at a glance.

The number of integers in the interval of −60 to 60 are 121 including 0, and further being added by one for "no measured value" and in total 122, which almost fully utilizes the information capacity of 128 (seventh power of 2) which can be expressed by 7 bits excluding an error bit, so that an electronic-storage medium can be effectively utilized.

In the conventional case, a measured value expressed by real numbers with decimals needed 8 bytes and in addition to it 2 real numbers for reference lower-limit value and upper-limit value and more for the description of a unit, and in total more than 30 bytes were needed, while a G-value requires only 1 byte corresponding to the storage capacity for one alphabetical character in a computer.

Further, from an idea that the information quantity which can be transformed into 1 byte, and all values inside the reference interval can be made 1 digit, the second system, mentioned in the above {(−63, 63), (−9, 9)} is considered.

When such an expression system of G-values as integers between −60 and 60 is used, the data in the past of a patient can be stored in an IC card; which will give hope for realizing such a system in which when a patient receives treatment of any doctor, he may be able to bring his data in the past stored in his IC card for reference.

What is claimed is:

1. A method for processing clinical numerical data, comprising the steps of:

arbitrarily setting values corresponding to upper and lower normal threshold limits of a quantitative amount or concentration of an analyte of a subject, as respective equal positive and negative integers, to thereby define a range of normal quantitative analyte values whereby a lower limit normal quantitative value of said analyte corresponds to said negative integer, and an upper limit normal quantitative value of said analyte corresponds to said positive integer, wherein the average of all values in said range is zero;

transforming observed quantitative measurements of said analyte from a particular subject into corresponding integers in accordance with said range defined by said upper and lower normal threshold limit integers;

associating specific values of said transformed observed quantitative measurements of said analyte with specific diagnoses; and displaying said transformed quantitative measurement integers, whereby a clinician can automatically reach a diagnosis of said subject with respect to said quantitative measurement of said analyte, by observing said displayed transformed quantitative measurement integers.

2. A method as set forth in claim 1, wherein the step of transforming comprises the steps of:

setting a lowest possible transformed value of an observed measurement to a first integer P, setting a highest possible transformed value of an observed measurement to a second integer Q, wherein said range falls between P and Q, with said upper normal threshold limit integer being referred to as $H_U$ and said lower normal threshold limit integer being referred to as $H_L$;

transforming observed quantitative measurements x according to one of the following transformation functions $H_1$, $H_2$, or $H_3$:

$$H_1(x) = \frac{2A}{\pi} * \text{Tan}^{-1}\left\{\frac{T_U - T_L}{f(U) - f(L)} * f(x) + \frac{f(U) * T_L - f(L) * T_U}{f(U) - f(L)}\right\}$$

$$H_2(x) = A * \text{Tanh}\left\{\frac{Ath_U - Ath_L}{f(U) - f(L)} * f(x) + \frac{f(U) * Ath_L - f(L) * Ath_U}{f(U) - f(L)}\right\}$$

$$H_3(x) = \frac{1}{2} * \left\{\left|\frac{H_U - H_L}{f(U) - f(L)} * \left[f(x) - \frac{f(U) + f(L)}{2}\right] - Q\right| - \left|\frac{H_U - H_L}{f(U) - f(L)} * \left[f(x) - \frac{f(U) + f(L)}{2}\right] - P\right|\right\} + B$$

where A and B are constants expressed by A=(P−Q)/2 and B=(P+Q)/2;

f(x) is an arbitrary monotonously increasing function;

$T_U = \text{Tan}\{\Pi*(H_U - B)/(2A)\}$;

$T_L = \text{Tan}\{\Pi*(H_L - B)/(2A)\}$;

$Ath_U = \text{Tanh}^{-1}\{(H_U - B)/A\}$; and $Ath_L = \text{Tanh}^{-1}\{(H_L - B)/A\}$.

3. A method as set forth in claim 1, wherein said display step further comprises the steps of assigning different colors to respective ranges of transformed quantitative measurement integers of different clinical significance, and displaying said transformed quantitative measurement integers in said assigned colors on a display.

4. A computer-readable storage medium having computer-executable instructions stored therein for causing a computer programmed with said instructions to process clinical numerical data, said instructions including instructions for:

arbitrarily setting values corresponding to upper and lower normal threshold limits of a quantitative amount or concentration of an analyte of a subject, as respective equal positive and negative integers, to thereby define a range of normal quantitative analyte values whereby a lower limit normal quantitative value of said analyte corresponds to said negative integer, and an upper limit normal quantitative value of said analyte corresponds to said positive integer, wherein the average of all values in said range is zero;

transforming observed quantitative measurements of said analyte from a particular subject into corresponding integers in accordance with said range defined by said upper and lower normal threshold limit integers;

associating specific values of said transformed observed quantitative measurements of said analyte with specific diagnoses; and displaying said transformed quantitative measurement integers, whereby a clinician can automatically reach a diagnosis of said subject with respect to said quantitative measurement of said analyte, by observing said displayed transformed quantitative measurement integers.

5. The computer-readable storage medium as set forth in claim 4, further comprising computer-executable instructions for assigning different colors to respective ranges of transformed quantitative measurement integers of different clinical significance, and for displaying said transformed quantitative measurement integers in said assigned colors on a display.

* * * * *